(12) United States Patent
Johnson

(10) Patent No.: US 6,613,067 B1
(45) Date of Patent: Sep. 2, 2003

(54) BALLOON PROTECTOR

(75) Inventor: Michael W. Johnson, Rogers, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 215 days.

(21) Appl. No.: 09/587,769

(22) Filed: Jun. 6, 2000

(51) Int. Cl.[7] ............................ A61M 29/00; A61F 2/06
(52) U.S. Cl. ............. 606/194; 604/103.11; 604/103.14; 623/1.12
(58) Field of Search ................. 604/96.01, 264, 604/265, 500, 507, 508, 509, 95–96, 164, 103.11, 103.14; 606/191, 108, 192, 194, 195; 623/1.1, 1.11, 1.12

(56) References Cited

U.S. PATENT DOCUMENTS

| | | | |
|---|---|---|---|
| 4,702,252 A | * 10/1987 | Brooks et al. | 604/103 |
| 4,796,629 A | * 1/1989 | Grayzel | 606/194 |
| 4,846,174 A | * 7/1989 | Willard et al. | 604/95 |
| 4,921,479 A | 5/1990 | Grayzel | |
| 5,015,231 A | 5/1991 | Keith et al. | |
| 5,053,007 A | 10/1991 | Euteneuer | |
| 5,066,298 A | 11/1991 | Hess | 606/194 |
| 5,137,512 A | 8/1992 | Burns et al. | 604/96 |
| 5,211,654 A | * 5/1993 | Kaltenbach | 606/194 |
| 5,334,146 A | * 8/1994 | Ozasa | 606/194 |
| 5,352,236 A | 10/1994 | Jung et al. | 606/194 |
| 5,417,707 A | 5/1995 | Parkola | 606/194 |
| 5,425,710 A | * 6/1995 | Khair et al. | 606/194 |
| 5,443,495 A | * 8/1995 | Buscemi et al. | 606/191 |
| 5,556,383 A | * 9/1996 | Wang et al. | 606/194 |
| 5,569,294 A | 10/1996 | Parkola | 606/194 |
| 5,613,979 A | * 3/1997 | Trotta et al. | 606/194 |
| 5,735,859 A | 4/1998 | Fischell et al. | 606/108 |
| 5,807,327 A | * 9/1998 | Green et al. | 604/96 |
| 5,868,707 A | 2/1999 | Williams et al. | 604/103 |
| 5,893,868 A | 4/1999 | Hanson et al. | 606/198 |
| 5,961,536 A | * 10/1999 | Mickley et al. | 606/194 |
| 5,968,069 A | * 10/1999 | Dusbabek et al. | 604/96.01 |
| 5,993,424 A | * 11/1999 | Lorenzo et al. | 604/164 |
| 6,110,146 A | 8/2000 | Berthiaume et al. | |
| 6,124,007 A | * 9/2000 | Wang et al. | 606/192 |
| 6,132,450 A | 10/2000 | Hanson et al. | 606/198 |
| 6,152,944 A | * 11/2000 | Holman et al. | 604/96.01 |
| 6,159,244 A | 12/2000 | Suddaby | |
| 6,168,617 B1 | * 1/2001 | Blaeser et al. | 623/1.11 |
| 6,168,748 B1 | * 1/2001 | Wang et al. | 606/194 |
| 6,176,849 B1 | * 1/2001 | Yang et al. | 604/265 |
| 6,447,540 B1 | * 9/2002 | Fontaine et al. | 623/1.12 |
| 2001/0001128 A1 | * 5/2001 | Holman et al. | 623/1.11 |
| 2002/0032406 A1 | * 3/2002 | Kusleika | 606/192 |

* cited by examiner

*Primary Examiner*—Thomas Denion
*Assistant Examiner*—Thai-Ba Trieu
(74) *Attorney, Agent, or Firm*—Vidas, Arrett & Steinkraus P.A.

(57) ABSTRACT

A method and apparatus for protecting a balloon of a balloon catheter from damage prior to inserting the balloon catheter into a body lumen. The balloon protector comprising a tube of synthetic material having a reduced inside diameter which is drawn about the catheter balloon. The balloon protector retaining the catheter in a reduced configuration. The material of the balloon protector including a kinked portion which provides the protector with an area that will draw inward toward and against the catheter when the ends of the protector are drawn longitudinally in opposite directions.

13 Claims, 3 Drawing Sheets

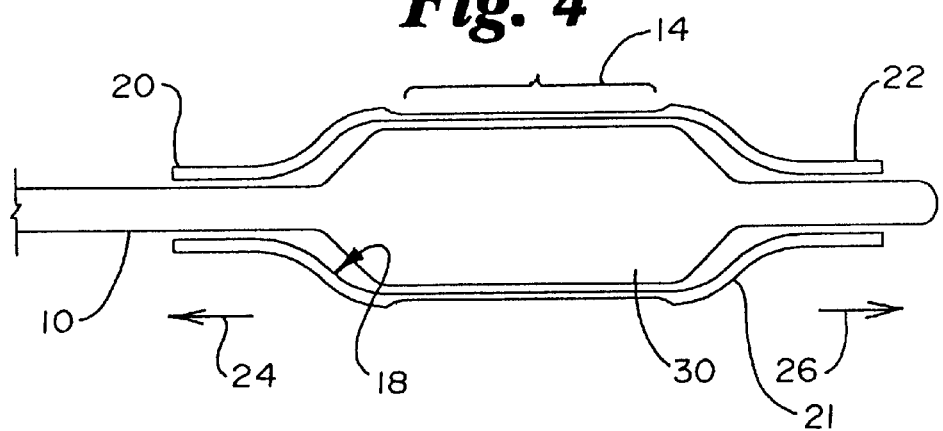
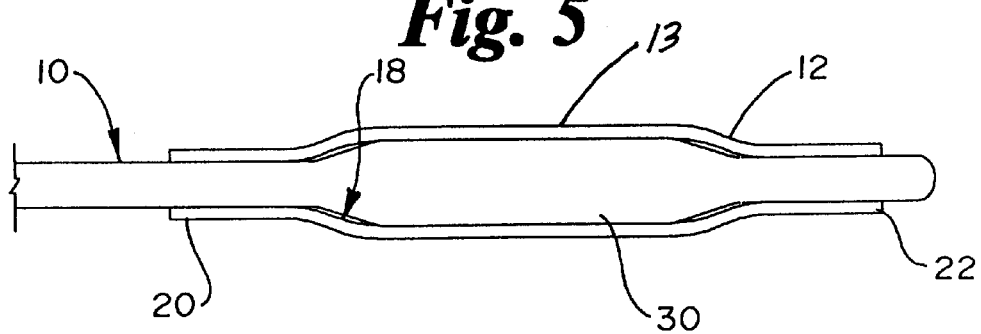
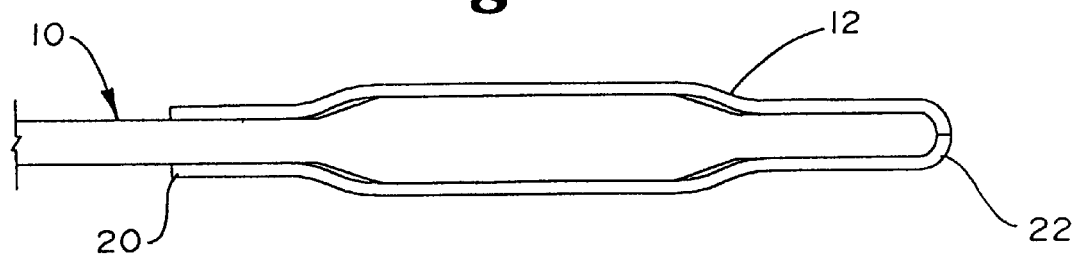

BALLOON PROTECTOR

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter. In typical PTCA procedures, the cardiovascular system of a patient is accessed with an introducer, usually in the groin area. All other devices including a guiding catheter are percutaneously introduced into the cardiovascular system of a patient through the introducer and advanced through a vessel until the distal end thereof is at a desired location in the vasculature. A guide wire and a dilatation catheter having a balloon on the distal end thereof are introduced through the guiding catheter with the guide wire sliding through the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with a fluid at relatively high pressures, such as greater than about four atmospheres, to radially compress the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, called a stent, inside the artery at the lesion. In general, stents are prosthetic devices which can be positioned within a body cavity, for example, a blood vessel of the body of a living human or in some other difficulty accessible place. A stent generally has a diameter which may be increased or decreased. Stents are particularly useful for permanently widening a vessel which is in a narrowed state, or for internally supporting a vessel damaged by an aneurysm.

Such stents are typically introduced into the body cavity by use of a catheter. The catheter is usually of the balloon catheter type in which the balloon is utilized to expand the stent, which is positioned over the balloon, to place it in a selected location in the body cavity. The stent is expanded to a larger diameter for placement in the vasculature, often by the balloon portion of the catheter.

One important characteristic of a dilatation balloon catheter is its "profile", which is determined by the outer diameter (O.D.) of the distal end portion of the balloon and stent when deflated. The outer diameter affects the ease and ability of the dilatation catheter to pass through a guide catheter, through the coronary arteries, and across a tight lesion.

Minimization of "profile" is of importance in balloon catheters and stent delivery systems. Accordingly, the present invention is particularly directed to a novel balloon protector which retains the balloon catheter in a reduced configuration prior to insertion of the catheter into a body lumen. The balloon protector of the present invention is suitable for use with a balloon catheter equipped with or without a stent.

A second important characteristic of a dilation balloon catheter is preventing damage to the catheter prior to insertion. It is known in the percutaneous balloon delivery art that the balloon or inflatable portion of a catheter may be easily damaged or ruptured prior to insertion into the body. Furthermore, preparation and associated manipulation of the balloon and /or stent prior to catheter insertion may impair balloon performance and possibly compromise the otherwise sterile condition of the catheter surface.

Protecting the catheter, especially the balloon, from damage and maintaining a sterile field about the catheter prior to insertion is of significant importance in any medical procedure involving a catheter. Accordingly the present invention is also directed to a novel balloon protector which has sufficiently strong and thick walls to protect the balloon from damage such as accidental puncture and that may be fitted over a balloon catheter with or without a stent, immediately after manufacturing and preparing the catheter for use.

BRIEF SUMMARY OF THE INVENTION

The present invention is directed to a balloon protector for use an a variety of balloon catheter types. More specifically, the present invention is directed to a protector tube having a pre-kinked portion. A sterile balloon catheter is drawn through a die containing the tube, the ends of the tube are then drawn outwardly thereby drawing the pre-kinked area of the tube down against the balloon catheter.

This invention provides for a diameter reducing balloon protector for use in shielding the various components of an implantable balloon catheter from damage such as puncture, as well as for providing the balloon catheter with a maintainable sterile field prior to use. The present balloon protector when drawn down about a balloon catheter has sufficient strength and thickness to maintain the balloon catheter (and an associated stent if desired) in a reduced configuration prior to inserting the catheter into a body lumen. The present balloon protector may be easily fitted to nearly any variety or size of balloon catheter with minimal cost and effort.

In order to provide the balloon protector with a means of being removed from the balloon catheter, the inside diameter of the balloon protector may be treated with a variety of lubrications such as a slip coat.

BRIEF DESCRIPTION OF THE SEVERAL VIEWS OF THE DRAWINGS

A detailed description of the invention is hereafter described with specific reference being made to the drawings in which:

FIG. 4 is a side view of the balloon protector and balloon catheter of FIG. 1 shown during the outward pulling of the tube ends;

FIG. 5 is a side view of the balloon protector and balloon catheter of FIG. 5 shown subsequent to the tube ends being drawn to a predetermined extent;

FIG. 6 is side view of another embodiment of the balloon protector;

DETAILED DESCRIPTION OF THE INVENTION

The present balloon protector may typically be constructed from extrudable materials such as polyether-polyester block copolymers. Preferably, the balloon protector is constructed from Arnitel® EM-740, however other materials which provide the necessary protective qualities and draw down capabilities as described in detail below, may also be used.

Whatever material is selected for use, the material will typically be extruded directly in tubular form or will be extruded as a film which may then be shaped into a tube. The diameter of the tube will have an inside diameter substantially equal to or larger than the outside diameter of a balloon catheter and its associated devices, such as a stent, in the pre-insertion or reduced configuration. Where the tube is extruded directly as a tube, the tube may be affixed to a die, the die provides a guide for inserting the balloon catheter into the tube. Where the material is a sheet or film, the material may be formed into a tube directly around the balloon catheter.

Figure 1:
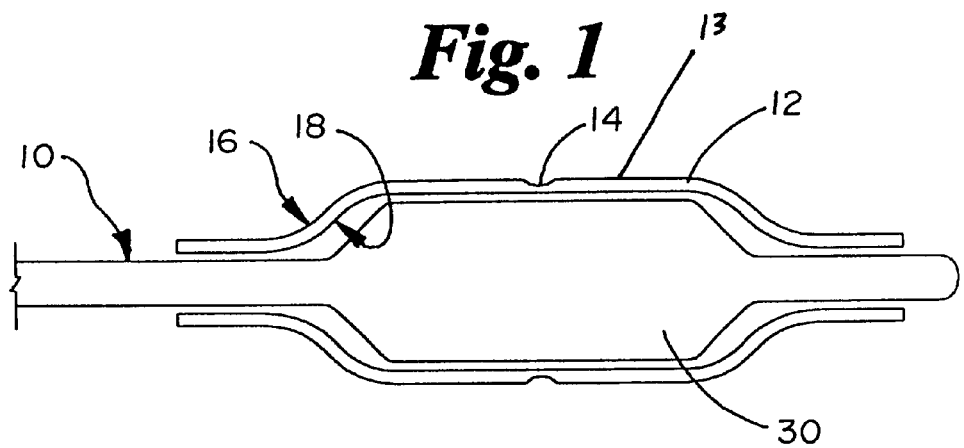
FIG. 1 is a side view of the balloon protector tube immediately after a balloon catheter has been inserted therein.

FIG. 1 shows a balloon catheter 10 within the tubular balloon protector 12 prior to drawing the balloon protector down.

The catheter 10 includes an inflatable portion or balloon 30 which has been folded into the pre-insertion or reduced configuration. In an alternative embodiment the catheter 10 may be configured for delivery of a stent or other device.

Figure 2:
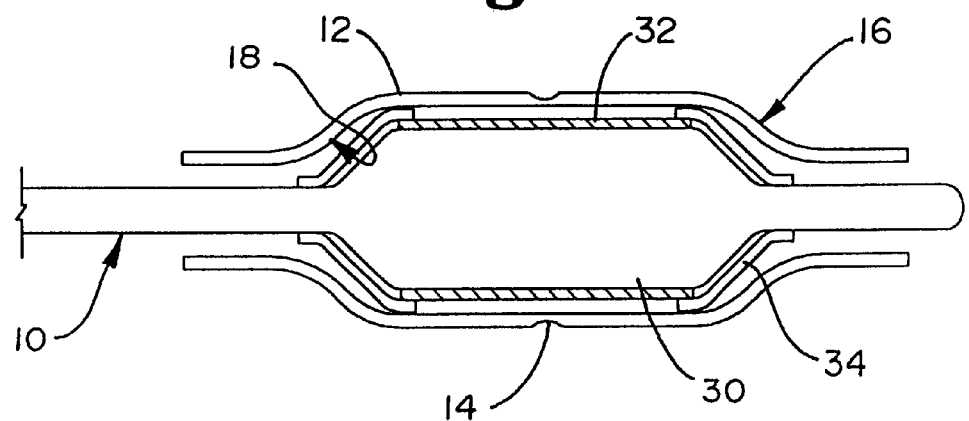
FIG. 2 is a side view of the balloon protector tube of FIG. 1 wherein the catheter is equipped with a balloon expandable stent.

In the embodiment shown in FIG. 2 the catheter includes a stent 32 as well as a pair of stent retaining sleeves 34. The catheter could also be configured for delivery of a self-expanding stent 32, and include a stent retaining sheath 36 and a pull back member 38 such as may be seen in FIG. 3.

In the various embodiments of the present invention, prior to inserting the catheter 10 into the tube 12, the outside surface of the catheter 10, the inside diameter 18 of the tube 12, or both surfaces in combination are treated with a lubrication. In a preferred embodiment both the catheter 10 and the inside diameter 18 have a slip coat applied prior to insertion of the catheter 10 into the tube 12. The addition of lubrication to the catheter or tube allows the balloon protector to be more readily removed from the catheter, by sliding the balloon protector distally off of the catheter prior to insertion of the catheter into a body vessel. The lubrication is preferably biocompatible.

Figure 3:
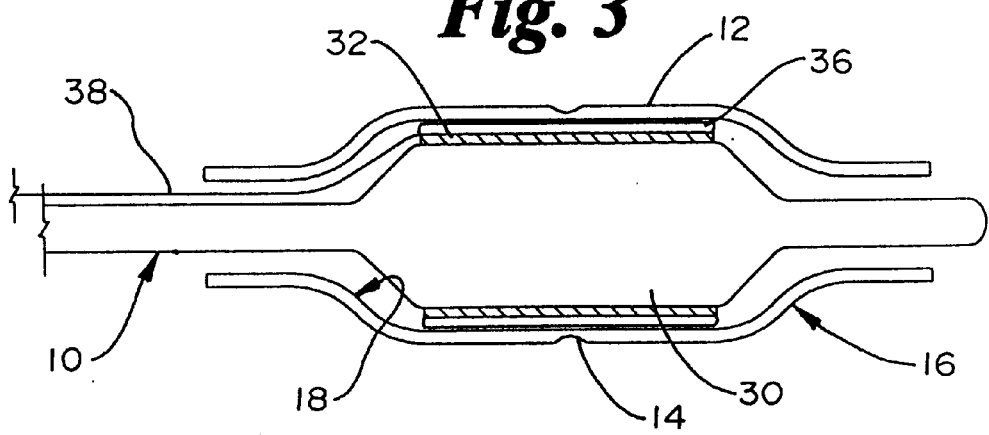
FIG. 3 is a side view of the balloon protector tube of FIG. 1 wherein the catheter is equipped with a self-expanding stent.

As may be seen in FIGS. 1–3, the balloon protector 12 includes a kinked or deformed area 14 which in the embodiment shown defines a radial 'V' around a portion of the balloon protector's outside diameter 16. A wide variety of methods may be incorporated to produce the kinked area 14, such as through the application of a kinking tool as is known in the art. If desired, the kinked area 14 could alternatively be placed on the inside diameter 18 of the protector 12 or both the inside 18 and outside 16 diameters. The only requirement of the method selected is that it produce a 'kink' which provides a localized weakening in the wall of the protector 12. Some examples of methods which could be used to form the kink 14 may include: mechanical kinking such as by forming a shallow incision with a bladed device around the tube and/or the momentary application of depressive force at the desired location such as with a clamping tool; hand kinking by simply bending the tube at the desired location; thinning the desired area of the tube where the kink is to be formed in the extrusion process; or even heat treating the specific area of the protector to weaken the wall as desired. Other methods of forming the kink 14 may be known, such methods may also be used to form the kinked area as desired.

Preferably, the kink 14 is made at any time prior to placing the protector 12 over the balloon catheter 10. More preferably, the kink 14 is made during the process of manufacturing of the protector 12.

As previously stated, the kinked area 14 provides a localized and uniform weakening of the protector 12. Once the reduced catheter 10 has been inserted into the balloon protector 12, the protector may be drawn down. The protector may be drawn down in a number of ways. As may be seen in the embodiment shown in FIG. 4, the ends 20 and 22 of the protector 12 are pulled or drawn outwardly. End 20 is pulled proximally and end 22 is pulled distally away from the balloon 30 with a uniform rate and force as indicated by arrows 24. As the ends 20 and 22 are pulled, the kinked area 14 will expand longitudinally and draw radially inward (i.e. draw down) toward the catheter 10.

Figure 7:
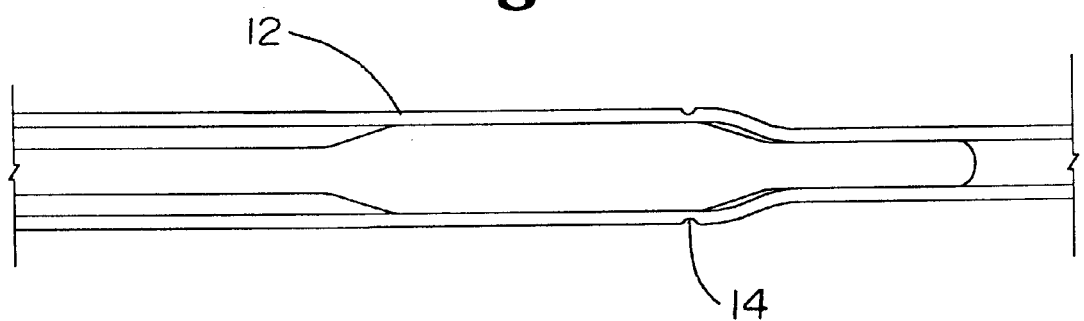
FIG. 7 is a side view of an embodiment of the balloon protector and balloon catheter of FIG. 1 shown during the outward pulling of a tube end.
Figure 8:
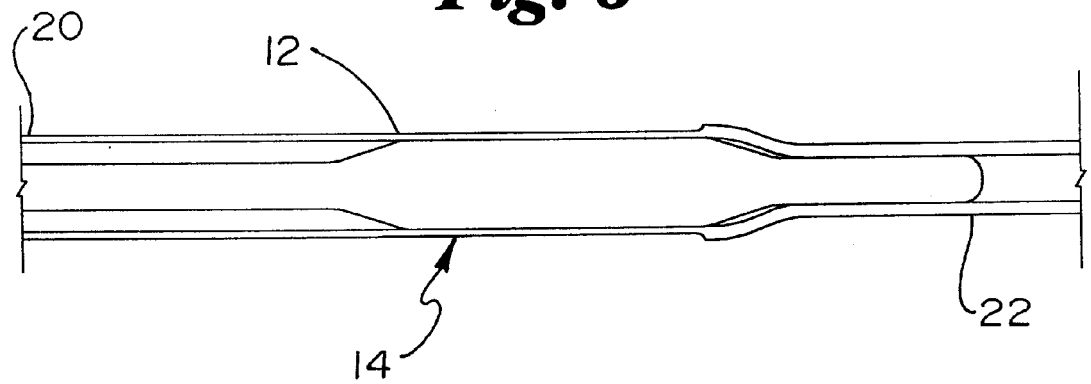
FIG. 8 is a side view of the balloon protector and balloon catheter of FIG. 7 shown subsequent to the tube end being drawn to a predetermined extent.

Alternatively, the protector 12 may be kinked at or near either end 20 or 22, such as is end 22 shown, in FIG. 7. The remaining end 20 of the protector 12 is then secured or otherwise immobilized about the catheter 10. The end 22 may be pulled or drawn outwardly away from the balloon 30 as indicated by arrow 24. When the end of the protector 12 includes the kinked area 14 and the end is then pulled in the appropriate direction away from the balloon 30, the kinked area 14 will propagate in the direction opposite the direction of the pull. The drawn down profile of the protector 12 which is the result of the propagation of the kinked area 14 may best be seen in FIG. 8, which shows the completed propagation of the kinked area 14 throughout the length of the protector 12.

The extent of the draw down of the kinked area may be best expressed as a percentage based on the ratio of the starting inside diameter 18 of the protector tube 12 prior to pulling ends 20 and 22, such as shown in FIG. 1; verses the inside diameter 18 after the ends 20 and 22 are pulled to a predetermined extent and at a predetermined rate, such as shown in FIG. 5. The draw down ratio of the balloon protector 12 may range from 5% to 60%.

The most significant factor which affects the extent of the draw down is the thickness of the tube walls 13. The wall thickness may range from 0.001 to 0.05 inches.

The rate at which the ends 20 and 22 are pulled also affects the extent of the draw down. In order to achieve a consistent and effective draw down percentage, an end of the protector 12 or, the ends 20 and 22 must be pulled at a constant rate. However, if the rate of pull on ends 20 and 22 is increased, it may be possible to increase the draw down percentage by as much as 3–10 percent than the draw down percentage would otherwise be. A constant pull rate is desirable, in that it provides a draw down with predictable characteristics and which will ensure that the protector wall is not torn or ruptured during the pulling process.

As may be seen in FIG. 5, when the ends 20 and 22 have been pulled at the proper rate for a desired amount of time, the inside diameter 18 of the protector 12 will be drawn down against the catheter 10. The present balloon protector 12 has a sufficient draw down percentage and inherent radial strength to contact and retain balloon catheter 10 in the reduced state.

When the balloon protector is drawn to the desired extent any excess tube material at the distal end 22 of the tube 12 which exceeds the length of the catheter 10 may be trimmed away.

In the embodiment shown in FIG. 6, the balloon protector 12 may assist in maintaining a sterile environment about the balloon protector. In this embodiment the distal end 22 has been closed and sealed. The balloon protector end 22 may be sealed such as by application of an adhesive to the inner diameter 18 of end 22 or by simply heat sealing the same. Other methods of sealing a tube are known in the art and may used as well as those described herein.

The remaining balloon protector material, most notably end 20, will retain sufficient tension around the catheter 10 to remain in place subsequent to the pulling stage described above.

In all of the various embodiments shown and described above, the balloon protector 12 provides the catheter 10 with a protective shield of resilient and flexible material which helps to prevent damage to the balloon catheter prior to use.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative arid not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A balloon protector comprising a tube of synthetic material, the tube having an unreduced state and a reduced state, the tube having an inside diameter and an outside diameter, the inside diameter having a catheter inserted therein, the catheter including an inflatable portion, at least the outside diameter of the tube having a kinked portion, the tube further having a proximal end and a distal end, in the reduced state at least a portion of the inside diameter of the tube which corresponds to the kinked portion of the tube being drawn inwardly down and about at least the expandable portion of the catheter and retaining the catheter in a reduced configuration, the tube constructed and arranged to be placed in the reduced state by pulling at least one end of the tube longitudinally in a direction away from at least the expandable portion of the catheter.

2. The balloon protector of claim 1 further comprising a lubricant, the lubricant applied to the inside diameter of the tube.

3. The balloon protector of claim 1 further comprising a lubricant, the lubricant applied to the catheter.

4. The balloon protector of claim 1 further comprising a lubricant, the lubricant applied to the inside diameter of the tube and the catheter.

5. The balloon protector of claim 4 wherein the lubricant is a slip coat.

6. The balloon protector of claim 1 wherein the catheter further comprises one or more implantable devices.

7. The balloon protector of claim 6 wherein the one or more implantable devices is a stent.

8. The balloon protector of claim 1 wherein the tube has a thickness of 0.001 to 0.05 inches.

9. The balloon protector of claim 1 wherein the portion of the tube being drawn down and about at least the expandable portion of the catheter is drawn down 5 to 60 percent relative to the portion of the tube which is not drawn down.

10. The balloon protector of claim 1 wherein the tube is constructed from one or more polyether-polyester block copolymers.

11. The balloon protector of claim 1 wherein the tube is constructed from Arnitel EM-740.

12. A method for protecting a balloon catheter comprising the steps of:

providing a tube constructed from one or more polyether-polyester block copolymers, the tube having an inside diameter and an outside diameter, the tube having a proximal end and a distal end;

kinking a predetermined area of the tube;

inserting a catheter within the inside diameter of the tube, the catheter having a proximal catheter end and a distal catheter end, the catheter further having at least one inflatable portion at the distal catheter end;

drawing the predetermined area of the tube inward toward and against the catheter by pulling at least one end of the tube longitudinally in a direction away from the inflatable portion of the catheter, at a predetermined rate, for a predetermined length of time.

13. The method for protecting a balloon catheter of claim 12 further comprising the step of:

trimming the distal end of the tube which exceeds the distal catheter end, and sealing the distal end of the tube.

* * * * *